United States Patent [19]

Yonan

[11] 4,069,221

[45] Jan. 17, 1978

[54] 1-(1-NAPHTHOXY)-3-(4-SUBSTITUTED-PIPERIDINO)-2-PROPANOLS

[75] Inventor: Peter K. Yonan, Morton Grove, Ill.

[73] Assignee: G. D. Searle & Co., Chicago, Ill.

[21] Appl. No.: 745,317

[22] Filed: Nov. 26, 1976

Related U.S. Application Data

[63] Continuation-in-part of Ser. No. 585,355, June 9, 1975, abandoned.

[51] Int. Cl.$^2$ .................. C07D 211/62; C07D 211/64
[52] U.S. Cl. .......................... 260/293.62; 260/348.51; 260/348.63
[58] Field of Search .................................. 260/293.62

[56] References Cited

U.S. PATENT DOCUMENTS 3,674,799  7/1972  Edenhofer et al. ........... 260/294.8 F Primary Examiner—Henry R. Jiles
Assistant Examiner—Richard A. Schwartz
Attorney, Agent, or Firm—Dragan J. Karadzic

[57] ABSTRACT 1-(1-naphthoxy)-3-(4-substituted-piperidino)-2-propanols, preparable by reacting 1,2-epoxy-3-(1-naphthoxy)-propane with the appropriate 4-substituted piperidine, are disclosed. The compounds may be alternately prepared from 1-chloro-3-(1-naphthoxy)-2-propanol with the appropriate 4-substituted piperidine. The compounds are useful antiarrhythmic agents.

4 Claims, No Drawings

1-(1-NAPHTHOXY)-3-(4-SUBSTITUTED-PIPERIDINO)-2-PROPANOLS

This is a continuation-in-part of application Ser. No. 585,355, filed June 9, 1975, now abandoned.

The present invention relates to a group of 1-(1-naphthoxy)-3-(4-substituted-piperidino)-2-propanols. More particularly, the present invention relates to a group of compounds having the general formula

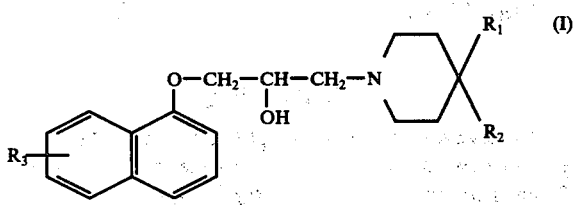

wherein $R_1$ is cyano or lower alkoxycarbonyl; $R_2$ is phenyl, p-chlorophenyl, and optionally, when $R_1$ is cyano, $R_2$ may be hydrogen; and $R_3$ is hydrogen, lower alkyl or halogen.

The lower alkoxycarbonyl groups referred to above contain 1 to 6 carbon atoms in the lower alkoxy portion and are exemplified by methoxycarbonyl, ethoxycarbonyl, propoxycarbonyl, isopropoxycarbonyl and the like. The lower alkyl groups likewise contain 1 to 6 carbon atoms and are illustrated by methyl, ethyl, propyl, isopropyl and the like. The halogen atoms include fluorine, chlorine, bromine and iodine.

Equivalent to the compounds of formula (I) for the purposes of this invention are the pharmaceutically acceptable acid addition and quaternary ammonium salts thereof. Such acid addition salts can be derived from a variety of organic and inorganic acids such as sulfuric, phosphoric, hydrochloric, hydrobromic, hydroiodic, sulfamic, citric, lactic, maleic, succinic, tartaric, cinnamic, acetic, benzoic, gluconic, ascorbic, and related acids. Similarly, the quaternary ammonium salts can be derived from a variety of organic esters of sulfuric, hydrohalic and aromatic sulfonic acids. Among such esters are methyl chloride and bromide, ethyl chloride, propyl chloride, butyl chloride, isobutyl chloride, benzyl chloride and bromide, phenethyl bromide, naphthylmethyl chloride, dimethyl sulfate, methyl benzenesulfonate, ethyl toluenesulfonate, ethylene chlorohydrin, propylene chlorohydrin, allyl bromide, methallyl bromide, and crotyl bromide.

The compounds of this invention are useful because of their pharmacological properties. In particular, they possess activity as anti-arrhythmic agents. Thus, they bring about a return to normal heart rhythm in animals in which the heart rhythm has become irregular.

The anti-arrhythmic utility of the instant compounds is evident from the results of a standardized test for their capacity to slow the ventricular tachycardia induced by aconitine in the isolated rabbit heart. The procedure is essentially that described by Lucchesi [J. Pharmacol. Exp. Therap., 137,291 (1962)], modified in certain particulars as follows: Hearts are obtained from adult albino rabbits of either sex and perfused in apparatus modeled after that devised by Anderson and Craver [J. Pharmacol. Exp. Therap., 93, 135 (1948)]. The composition of the perfusion solution is the same as Lucchesi's, but the volume is increased to 200 ml. and the temperature lowered to 28° C. Aconitine (ordinarily as the nitrate) is administered as soon as the heart beat is regular and the EKG pattern normal, the dose being so selected as to at least double the rate. Typically, 0.05 ml. of 0.1% aconitine nitrate in physiological saline is injected. EKG's are recorded at 5 minute intervals after onset of ventricular tachycardia until two successive readings show stabilization of the rate. Perfusate collected during this time is discarded and replaced with fresh solution q.s. 200 ml. Promptly following stabilization, 2 mg. of compound dissolved or suspended in 1 ml. of physiological saline is mixed with the perfusion solution. Ten minutes later a like amount is introduced, followed after a further ten minutes by double the first amount. Final concentration of compound in the perfusion solution is thus 40 mg. per liter. Recording of EKG's is continued at five minute intervals throughout this time and for 10 minutes thereafter. A compound is considered anti-arrhythmic if, at any time during the 30 minutes immediately following initial administration in at least half of a minimum of two tests, it reduces by 50% or more the rate recorded 10 minutes after onset of tachycardia. Among the compounds of this invention which have been found particularly active in this test are the representative compounds 3-(4-cyanopiperidino)-1-(1-naphthoxy)-2-propanol, 1-(1-naphthoxy)-3-(4-phenylpiperidino)-2-propanol, 3-(4-cyano-4-phenylpiperidino)-1-(1-naphthoxy)-2-propanol and 3-[4-(p-chlorophenyl)-4-ethoxycarbonyl-piperidino]-1-(1-naphthoxy)-2-propanol.

In view of their potent pharmacological properties, the compounds of this invention can be combined with pharmaceutical carriers and administered in a variety of well-known pharmaceutical forms suitable for oral or parenteral administration.

The compounds of the present invention may be conveniently prepared by contacting the appropriate 1,2-epoxy-3-(1-naphthoxy)propane of the formula

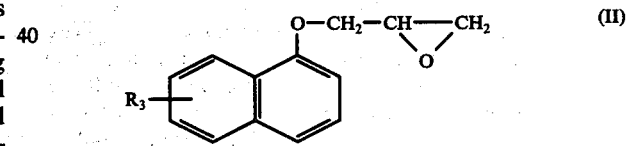

wherein $R_3$ is defined as hereinbefore with the appropriate 4-substituted piperidine of the formula

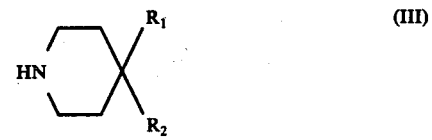

wherein $R_1$ and $R_2$ are defined as hereinbefore. Depending on the nature of the reactants, it is possible to carry out this reaction in the presence or absence of a solvent. The use of a solvent is, however, generally preferred. An especially desirable solvent is ethanol, while other possible solvents include methanol and isopropanol. Time and temperature are not critical factors for the conduct of this reaction, typical temperatures varying from room temperature to reflux and typical times being in the range of 30 minutes to several hours.

An alternate route for the synthesis of the subject compounds involves contacting the appropriate 1-chloro-3-(1-naphthoxy)-2-propanol of the formula

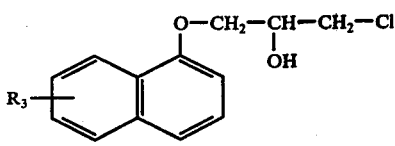

wherein R₃ is defined as hereinbefore, with the appropriate 4-substituted piperidine of formula (III). Again, depending on the nature of the reactants, it is possible to carry out this reaction in the presence or absence of a solvent. Suitable solvents include ketones, such as 2-butanone and acetone, aromatic hydrocarbons such as benzene and toluene, high boiling ethers such as dioxane, lower alkanols such as methanol and ethanol, dimethylformamide, and dimethylsulfoxide.

The starting material of formula (II) is conveniently prepared as detailed in *J. Am. Chem. Soc.*, 77, 3402-3 (1955). The preparation of the starting material of formula (IV) is described in *J. Chem. Soc.*, 1571 (1954).

The following examples describe in detail compounds illustrative of the present invention and methods which have been devised for their preparation. It will be apparent to those skilled in the art that many modifications, both of materials and methods, may be practiced without departing from the purpose and intent of this disclosure. Throughout the examples hereinafter set forth, temperatures are given in degrees centigrade (° C.) and relative amounts in parts by weight, except as otherwise noted.

EXAMPLE 1

A solution of 5.0 parts of 1,2-epoxy-3-(1-naphthoxy)-propane and 5.0 parts of 4-cyanopiperidine in 79 parts of ethanol is refluxed for 24 hours. The solution is then stripped of solvent under reduced pressure to give as a low melting solid, 3-(4-cyano-piperidine)-1-(1-naphthoxy)-2-propanol. The hydrochloride salt is then prepared by dissolving the solid in isopropanol and adding a solution of hydrochloric acid in isopropanol. The resulting salt is separated by filtration and crystallized from a mixture of ethanol and ethyl ether to give 3-(4-cyanopiperidino)-1-(1-naphthoxy)-2-propanol hydrochloride, melting at about 190°-192° C. and represented by the following structural formula

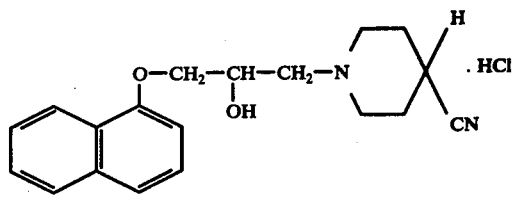

EXAMPLE 2

To a solution of 5.0 parts of 1,2-epoxy-3-(1-naphthoxy)propane in 79 parts of ethanol is added 5.0 parts of 4-phenylpiperidine. The resulting mixture is then refluxed for 24 hours. Evaporation of the solvent from the reaction mixture under reduced pressure affords 1-(1-naphthoxy)-3-(4-phenylpiperidino)-2-propanol. This free amine is then dissolved in isopropanol and treated with a solution of hydrochloric acid in isopropanol. The resulting salt is separated by filtration and recrystallized from a mixture of ethanol and ethyl ether to give 1-(1-naphthoxy)-3-(4-phenylpiperidino)-2-propanol hydrochloride. This compound melts at 195°-197° C. and is represented by the following structural formula

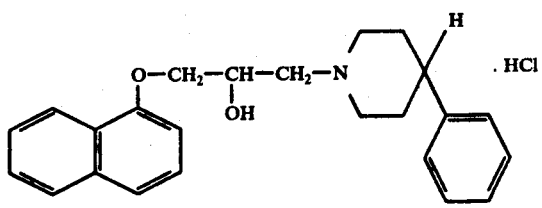

EXAMPLE 3

A solution of 5.0 parts of 1,2-epoxy-3-(1-naphthoxy)-propane and 5.0 parts of 4-cyano-4-phenylpiperidine in 79 parts of ethanol is refluxed for 24 hours. Evaporation of the solvent from the reaction mixture under reduced pressure affords 3-(4-cyano-4-phenylpiperidino)-1-(1-naphthoxy)-2-propanol. The hydrochloride salt is then prepared by addition of a solution of hydrochloric acid in isopropanol to an isopropanol solution of the free amine. The resulting salt is separated by filtration and recrystallized from isopropanol to afford 3-(4-cyano-4-phenylpiperidino)-1-(1-naphthoxy)-2-propanol hydrochloride, melting at 213°-215° C. and represented by the following structural formula

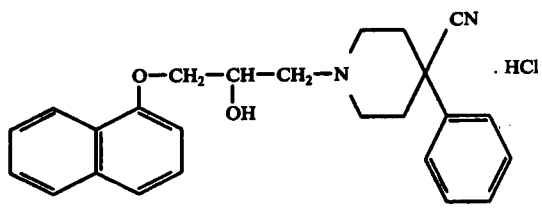

EXAMPLE 4

To a solution of 5.0 parts of 1,2-epoxy-3-(1-naphthoxy)propane in 79 parts of ethanol is added 5.0 parts of 4-(p-chlorophenyl)-4-ethoxycarbonylpiperidine. The resulting mixture is then refluxed for 24 hours. The solvent is stripped from the reaction mixture under reduced pressure to afford 3-[4-(p-chlorophenyl)-4-ethoxycarbonylpiperidino]-1-(1-naphthoxy)-2-propanol. This material is dissolved in isopropanol and treated with a solution of hydrochloric acid in isopropanol. The resulting salt is separated by filtration and recrystallized from a mixture of isopropanol and ethyl ether to give 3-[4-(p-chlorophenyl)-4-ethoxycarbonylpiperidino]-1-(1-naphthoxy)-2-propanol hydrochloride. This compound exhibits a melting point of 196°-198° C. and is represented by the following structural formula

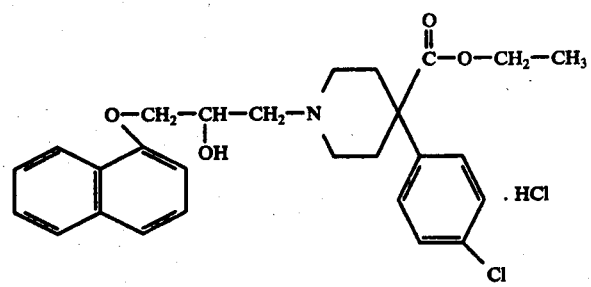

EXAMPLE 5

5.0 Parts of 1,2-epoxy-3-(1-naphthoxy)propane and 5.0 parts of 4-hydroxy-4-phenylpiperidine are dissolved in 79 parts of ethanol and refluxed for 24 hours. The resulting mixture is then stripped of solvent under reduced pressure to give 3-[4-(p-chlorophenyl)-4-hydroxypiperidino]-1-(1-naphthoxy)-2-propanol. The hydrochloride salt is prepared by dissolving this material in isopropanol and adding a solution of hydrochloric acid in isopropanol. The resulting salt is then filtered and recrystallized from a mixture of ethanol and ethyl ether to give 3-[4-(p-chlorophenyl)-4-hydroxypiperidino]-1-(1-naphthoxy)-2-propanol hydrochloride. This compound melts at 217°–219° C. and is represented by the following structural formula

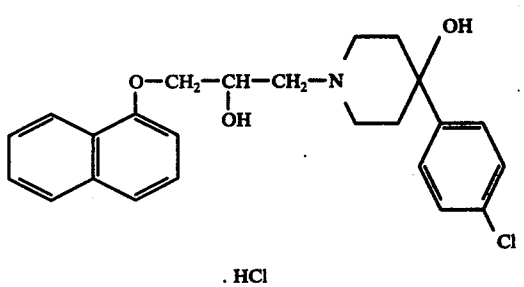

. HCl

EXAMPLE 6

4.0 Parts of 1-chloro-3-(1-naphthoxy)-2-propanol and 16.0 parts of 4-cyanopiperidine are heated in a sealed vessel for 10 hours at about 100° C. That reaction mixture is then diluted with 50 parts of water, acidified with concentrated hydrochloric acid, and extracted with 35 parts of ethyl ether. The aqueous phase is separated and made alkaline with the addition of 10 N sodium hydroxide. The resultant solid is filtered and converted to the hydrochloride salt by redissolving the solid in isopropanol and adding a solution of hydrochloric acid in isopropanol. The resulting salt is separated by filtration and crystallized from a mixture of ethanol and ethyl ether to give 3-(4-cyanopiperidino)-1-(1-naphthoxy)-2-propanol hydrochloride, identical to the product of Example 1.

What is claimed is:

1. A compound of the general formula

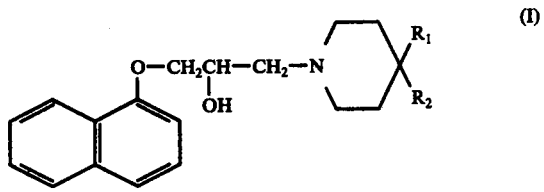

wherein $R_1$ is cyano, or lower alkoxycarbonyl, and $R_2$ is phenyl, p-chlorophenyl, and, optionally, when $R_1$ is cyano, $R_2$ may be hydrogen.

2. A compound according to claim 1 which is 3-(4-cyanopiperidino)-1-(1-naphthoxy)-2-propanol.

3. A compound according to claim 1 which is 3-(4-cyano-4-phenylpiperidino)-1-(1-naphthoxy)-2-propanol.

4. A compound according to claim 1 which is 3-[4-(p-chlorophenyl)-4-ethoxycarbonylpiperidino]-1-(1-naphthoxy)-2-propanol.

* * * * *